US009408474B2

(12) United States Patent
Rubey

(10) Patent No.: US 9,408,474 B2
(45) **Date of Patent: *Aug. 9, 2016**

(54) BUOYANT POOL LOUNGE CHAIR FRAME AND BUOYANT POOL LOUNGE CHAIR USING THE SAME

(71) Applicant: TRC Recreation, LP, Wichita Falls, TX (US)

(72) Inventor: Ulyss Ray Rubey, Graham, TX (US)

(73) Assignee: TRC Recreation, LP, Wichita Falls, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/858,520

(22) Filed: Sep. 18, 2015

(65) Prior Publication Data

US 2016/0007758 A1 Jan. 14, 2016

Related U.S. Application Data

(63) Continuation of application No. 14/330,733, filed on Jul. 14, 2014, now Pat. No. 9,139,263.

(60) Provisional application No. 61/846,436, filed on Jul. 15, 2013.

(51) Int. Cl.

| | |
|---|---|
| ***A47C 15/00*** | (2006.01) |
| ***B63B 35/74*** | (2006.01) |
| ***G01N 33/569*** | (2006.01) |

(52) U.S. Cl.

CPC ............... *A47C 15/006* (2013.01); *B63B 35/74* (2013.01); *G01N 33/56911* (2013.01); *G01N 2333/00* (2013.01); *G01N 2333/33* (2013.01)

(58) Field of Classification Search

CPC .................................................... A47C 15/006
USPC ................................................. 441/130–132
See application file for complete search history.

(56) References Cited

U.S. PATENT DOCUMENTS

| | | | | | |
|---|---|---|---|---|---|
| D169,366 | S | * | 4/1953 | Feldman ................ | A47C 15/74 297/452.22 |
| 3,067,441 | A | | 12/1962 | Dysard et al. | |
| 3,102,280 | A | | 9/1963 | Williams | |
| 3,860,976 | A | | 1/1975 | Suyama | |
| 3,984,888 | A | | 10/1976 | DeLano | |
| 4,358,866 | A | | 11/1982 | Rhodes | |
| 4,564,240 | A | | 1/1986 | Thieme | |
| 4,662,852 | A | * | 5/1987 | Schneider ............... | B63B 35/74 297/317 |
| 4,799,910 | A | | 1/1989 | Kellough | |
| 4,986,781 | A | * | 1/1991 | Smith ................. | A47C 15/006 4/541.3 |
| 5,004,296 | A | * | 4/1991 | Ziegenfuss, Jr. ..... | A47C 15/006 297/188.14 |

(Continued)

*Primary Examiner* — Lars A Olson
*Assistant Examiner* — Jovon Hayes
(74) *Attorney, Agent, or Firm* — Scott T. Griggs; Griggs Bergen LLP

(57) ABSTRACT

A buoyant pool lounge chair frame and buoyant pool lounge chair using the same are disclosed. In one embodiment of the buoyant pool lounge chair frame for supporting a floatation device while the buoyant pool chair frame is floating in water, a pod frame is provided including a rigid base portion and a window having a vertical opening therethrough. A substantially inverted parabolic surface is positioned at the front of the pod frame and a centra including a rigid back is positioned at the rear of the pod frame such that the window is therebetween. The pod frame is sized to accept a floatation device such that the substantially inverted parabolic surface and the centra engage the floatation device in a load-bearing relationship.

20 Claims, 4 Drawing Sheets

24 20 12 14 10 16 26 50 34 22 40 42 52 24 20 80 84 86 82 26 22 12 38 36 30 44

(56) References Cited

U.S. PATENT DOCUMENTS

| | | | | | |
|---|---|---|---|---|---|
| 5,088,723 | A | | 2/1992 | Simmons | |
| 5,403,220 | A | * | 4/1995 | Goad, Sr. | A47C 15/006 440/38 |
| 5,439,405 | A | * | 8/1995 | Storey | A45C 9/00 441/126 |
| 6,045,423 | A | * | 4/2000 | Silvia | B63B 35/78 441/130 |
| 6,086,150 | A | * | 7/2000 | Scheurer | A47C 15/006 297/219.1 |
| 6,126,504 | A | * | 10/2000 | Day | B63C 9/135 441/129 |
| 6,312,054 | B1 | * | 11/2001 | Scheurer | A47C 1/027 297/219.1 |
| 6,746,293 | B1 | * | 6/2004 | Kirby, Jr. | A47C 15/006 4/492 |
| 6,783,181 | B2 | | 8/2004 | Scheurer et al. | |
| 6,991,285 | B1 | * | 1/2006 | Hemenway | B60N 2/203 296/65.01 |
| 7,571,965 | B1 | * | 8/2009 | Perry | A47C 15/006 297/440.16 |

* cited by examiner

BUOYANT POOL LOUNGE CHAIR FRAME AND BUOYANT POOL LOUNGE CHAIR USING THE SAME

PRIORITY STATEMENT AND CROSS REFERENCE TO RELATED APPLICATIONS

This application is a continuation of U.S. patent application Ser. No. 14/330,733 filed on Jul. 14, 2014 in the name of Ulyss Ray Rubey, and issued on Sep. 22, 2015 as U.S. Pat. No. 9,139,263; which claims priority from U.S. Patent Application Ser. No. 61/846,436 entitled "Buoyant Pool Chair" and filed on Jul. 15, 2013 in the name of Ulyss Ray Rubey; which are hereby incorporated by reference for all purposes.

TECHNICAL FIELD OF THE INVENTION

This invention relates, in general, to swimming pool accessories and in particular to a buoyant pool lounge chair frame and a buoyant pool lounge chair utilizing the same for supporting a person in a seated position while the buoyant pool lounge chair frame is floating in water.

BACKGROUND OF THE INVENTION

Swimming pools offer personal recreation and relaxation in a variety of settings, including private homes, apartment complexes, motels, resorts, and country clubs. Various flotation devices including buoyant chairs, rafts, water wings, floating cushions, body floats and air mattresses are used by swimmers as an aid for floating and relaxing on the surface of the water, while remaining seated upright, reclining or lounging, either partially or completely submerged. These items of pool furniture include flotation cushions made of a buoyant material such as open cell foam, closed cell foam, cork, kapok, fiberglass or balsa wood, which are sealed within a protective outer covering. Special care should be taken in the construction of buoyant lounge chairs to provide sufficient buoyancy material to maintain a stable upright orientation while the occupant is an a semi-reclining or sitting orientation. The buoyant lounge chair may overturn in response to shifting of its center of buoyancy as the occupant turns or moves about and, as a result, there is a continuing need for improved design.

SUMMARY OF THE INVENTION

It would be advantageous to achieve a buoyant pool lounge chair frame and a buoyant pool lounge chair utilizing the same for providing support for a swimmer in an upright, semi-reclining or sitting position that would improve upon existing limitations in stability and functionality. It would also be desirable to enable a mechanical solution that would mitigate or eliminate the chances of the buoyant pool lounge chair being overturned in response to shifting of its center or buoyancy. Further, it would be desirable to enable a mechanical solution that provides a buoyant pool lounge chair while leveraging the use of existing pool floats. To better address one or more of these concerns, a buoyant pool lounge chair frame and a buoyant pool lounge chair frame utilizing the same are disclosed.

In one embodiment of the buoyant pool lounge chair frame for supporting a floatation device while the buoyant pool chair frame is floating in water, a pod frame is provided including a rigid base portion and a window having a vertical opening therethrough. A substantially inverted parabolic surface is positioned at the front of the pod frame and a centra including a rigid back is positioned at the rear of the pod frame such that the window is therebetween. The pod frame is sized to accept a floatation device such that the substantially inverted parabolic surface and the centra engage the floatation device in a load-bearing relationship. In an embodiment of the buoyant pool lounge chair, a pool float is releasably engageable with the buoyant pool lounge chair frame to provide a buoyant pool lounge chair. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
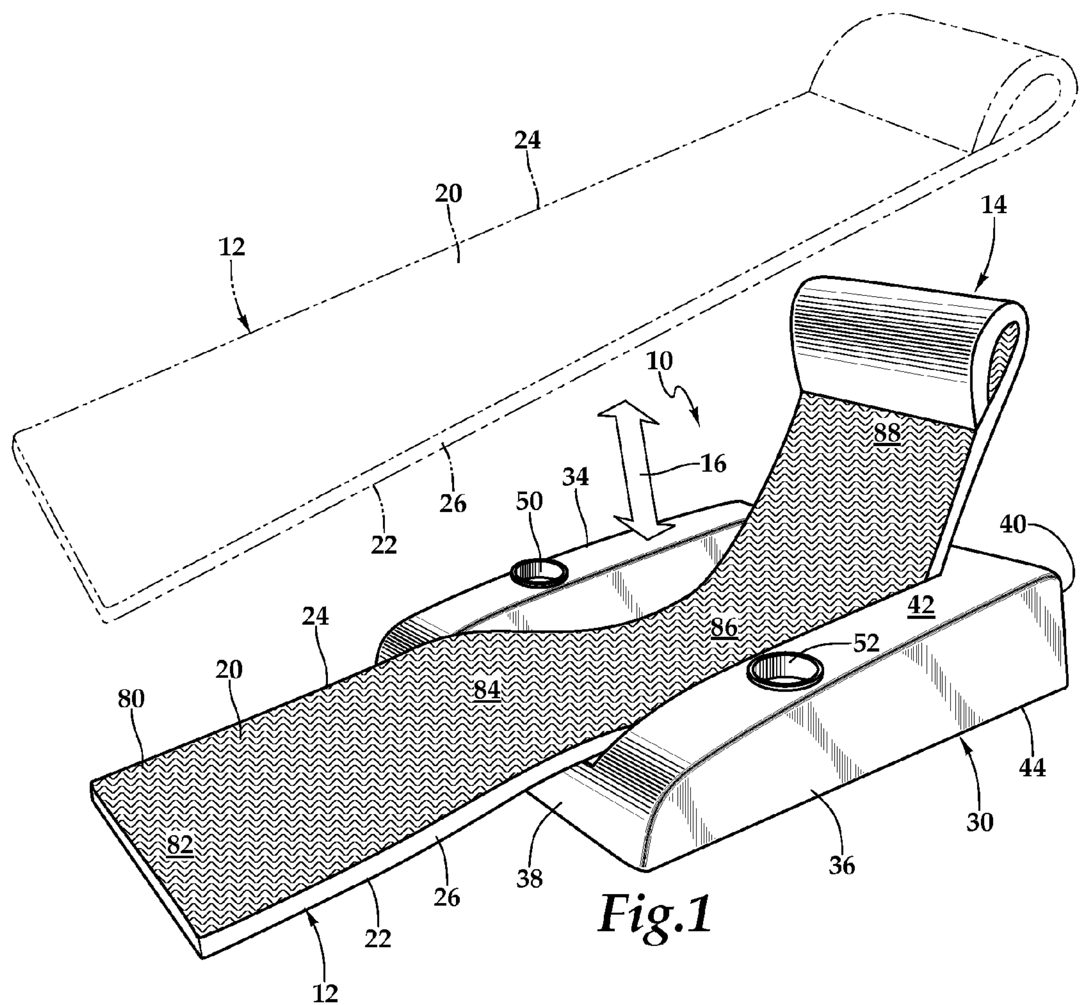
FIG. 1 is a front perspective view of one embodiment of a buoyant pool lounge chair frame being releasably engaged by a pool float according to the teachings presented herein to provide a buoyant pool lounge chair.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring now to FIG. 1 through FIG. 7, therein is depicted one embodiment of a buoyant pool lounge chair frame, which is schematically illustrated and designated 10. As shown, the buoyant pool lounge chair frame 10 engages a flotation device 12, depicted as a pool float, to provide a buoyant pool lounge chair 14 to support a person while the buoyant pool chair frame 10 is floating in water. The releasable engagement is depicted by arrow 16 in FIG. 1. Continuing with the description of FIG. 1 through FIG. 7, as illustrated, the floatation device 12 includes an upper side 20, a lower side 22, and edges 24, 26. In one implementation, the floatation device 12 is defined by a continuous form of pliable foam material. The floatation device 12 is designed to keep an individual afloat in a reclining position separate and apart from the buoyant pool lounge chair frame 10. In one implementation, the flotation device 12 is buoyant in water separate and apart from the buoyant pool lounge chair 14. In this manner, the buoyant pool lounge chair frame 10 presented herein leverages the use of an existing floatation device 12 to provide a buoyant pool lounge chair 14, which includes the buoyant pool lounge chair frame 10 and the flotation device 12.

With respect to the buoyant pool lounge chair frame 10, a pod frame 30 includes a rigid base portion 32 having a right side 34, a left side 36, a front support portion 38, and a rear support portion 40. The rigid base portion 32 of the pod frame 30 also includes a top surface 42 and a bottom surface 44. A waterproof coating 45 is applied to the rigid base portion 32. Right and left arm support members 46, 48 are respectively positioned at the right and left sides 34, 36 of the pod frame 30. The right and left arm support members 46, 48 may include respective cup holders 50, 52 positioned therein. In one embodiment, the front support portion 38 includes a substantially inverted parabolic surface 54 having a vertex at the top surface 42 opposite the bottom surface 44. As shown, the pod frame 30 is a substantially half-truncated pyramid having an acute scalene triangle profile 56 descending from the rear support portion 40 to the front support portion 38. A clipped end 58 is positioned proximate the front support portion 38 at the respective intersections of the right side 34 and the front support portion 38 and the left side 36 and the front support portion 38. In one embodiment, as shown, the clipped end 58 may take the form of a tapered clipped end.

As illustrated, the pod frame 30 includes a window 60 intersecting the right side 34, the left side 36, the front supporting portion 38 and the rear supporting portion 40 to provide a vertical opening 62 therethrough. The vertical opening 62 is configured and sized to accept a portion of the flotation device 12 therethrough. Front and rear cross-bars 64, 66 traverse the span between the right side 34 and left side 36 of the pod frame 30. It should be appreciated, however, that the number and placement of cross-bars may vary depending on the construction and application of the pod frame 30. In one implementation, as shown, the rear cross-bar 66 is at least partially exposed at void 67, which is within rear support portion 40, to provide a handle for carrying the buoyant pool lounge chair frame 10 or a hanging member from which the buoyant pool lounge chair frame 10 may be conveniently stored on an elevated position from a hook or other means. The floating stability of the buoyant pool lounge chair frame 10 is improved by the bulbous portion 68 of the rear support portion 40, which serves to bolster the floatation device 12 and any occupant therein. The bulbous portion 68 maintains the rear support portion 40 and, by extension, the pod frame 30 in a traverse orientation relative to the centra 70 as an individual may move within the floatation device 12, which is positioned thereon.

A centra 70 includes a rigid back support 72 positioned between the right side 34 and the left side 36 of the pod frame 30 and extending from the pod frame 30 proximate the rear support portion 40. In one implementation, the centra 70 forms an obtuse angle with a base of the rear support portion 40 at the bottom surface 44 of the rigid base portion 32 as shown by angle $\alpha$. Further, the centra 70 may provide a linear surface and be a concave surface conforming to the traverse curvature of the human spine. The centra 70 may be at least partially integrated with the rear support portion 40, fully integrated with the rear support portion 40, or releasably coupled to the rear support portion 40. In the illustrated embodiment, the centra 70 is releasably coupled, as shown by arrow 73, to the rear support portion 40 by a fastener and, in particular, a hook-and-loop fastener is utilized with corresponding hook-and-loop fasteners 74, 76 respectively secured to the face of the rear support portion 40 and the rear of the centra 70. As will be appreciated, by releasably engaging the centra 70 with the pod frame 30, the form factor of the buoyant pool lounge chair frame 10 may be further decreased for convenient storage and quickly and easily assembled when removed from storage for use.

Figure 2:
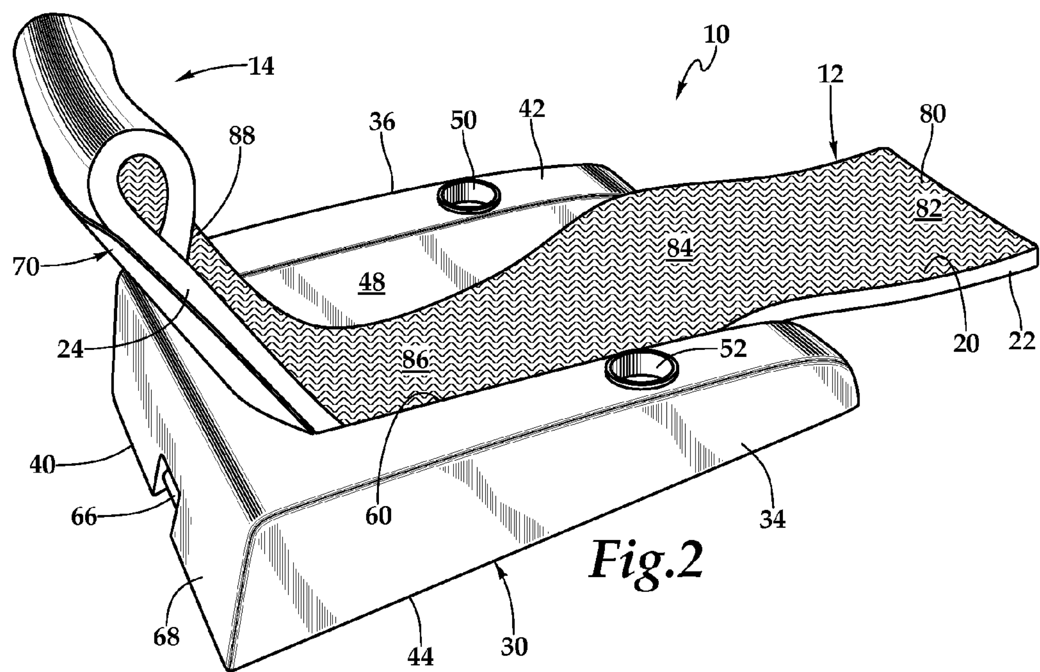
FIG. 2 is a rear perspective view on the buoyant pool lounge chair frame depicted in FIG. 1 having the pool float engaged therewith to provide a buoyant pool lounge chair.
Figure 3A:
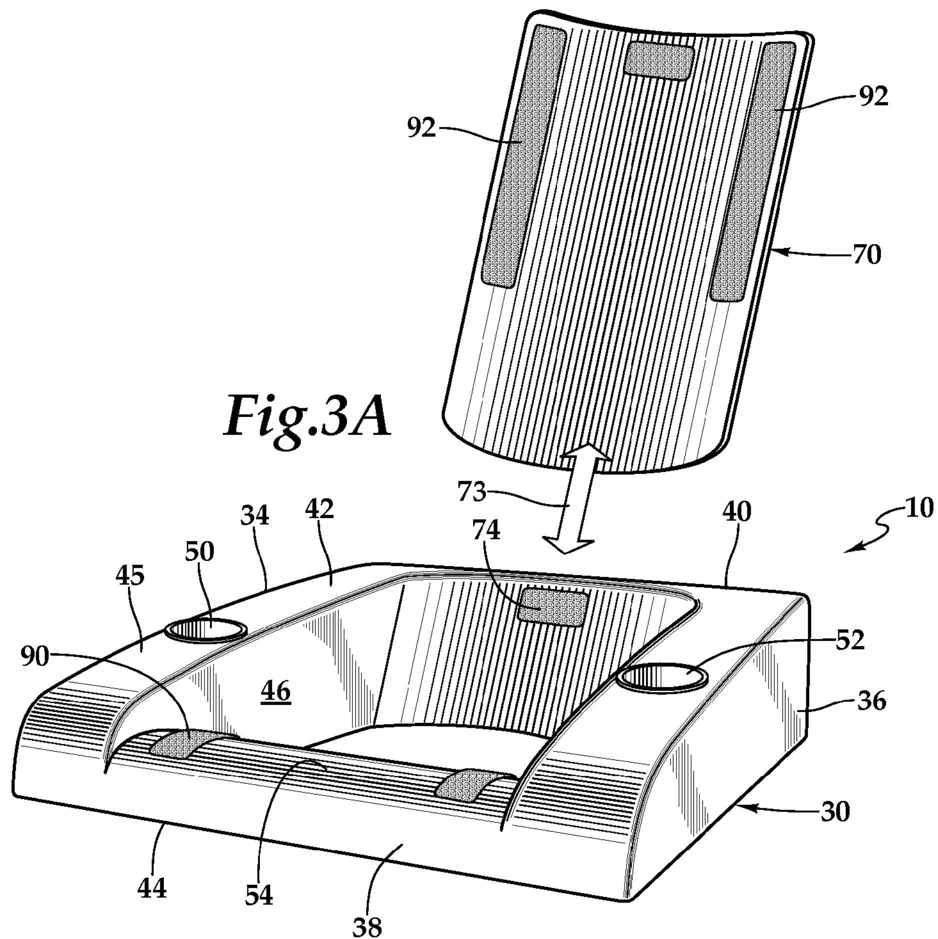
FIG. 3A is a front perspective view of one embodiment of the buoyant pool lounge chair frame depicted in FIG. 1 being assembled.
Figure 3B:
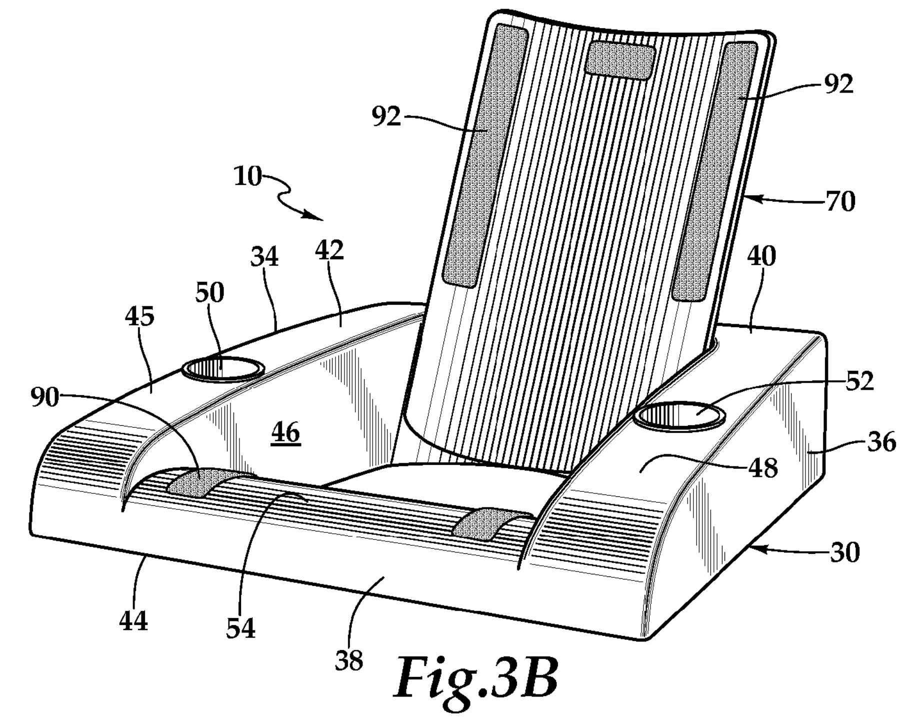
FIG. 3B is a front perspective view of the buoyant pool lounge chair frame depicted in FIG. 3A as assembled.
Figure 4A:
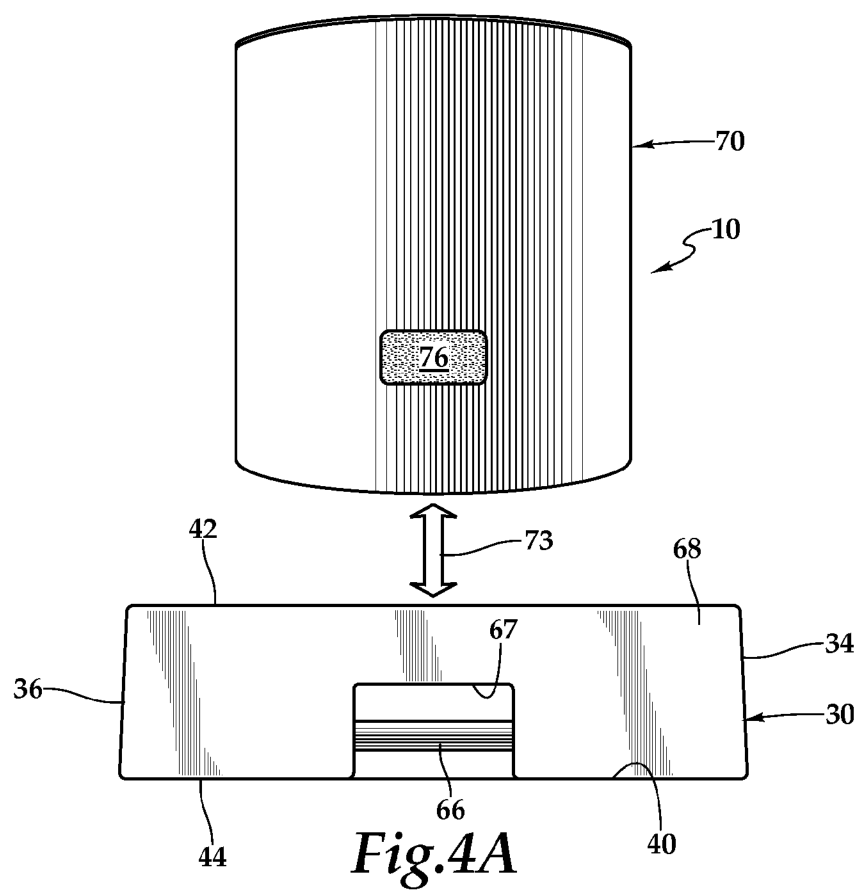
FIG. 4A is a rear elevation view of the buoyant pool lounge chair frame depicted in FIG. 3A.
Figure 4B:
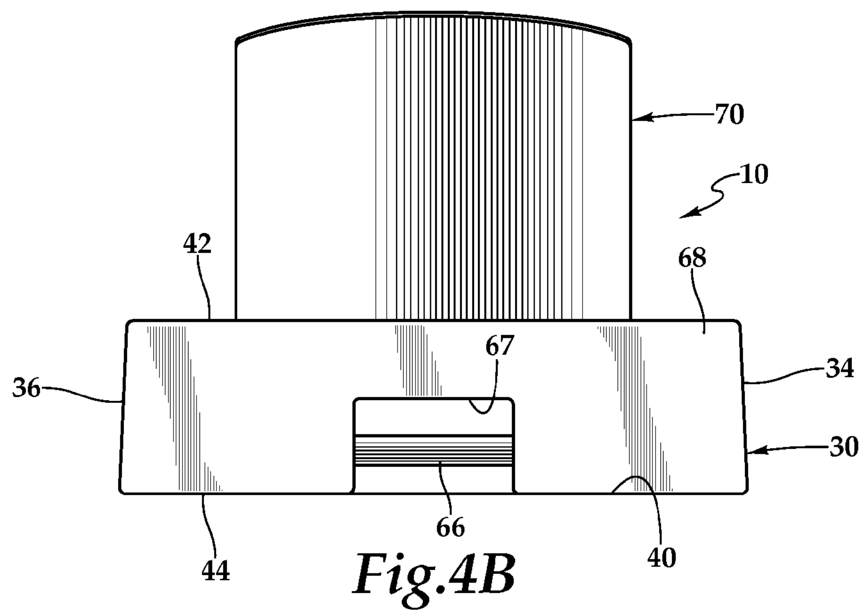
FIG. 4B is a rear elevation view of the buoyant pool lounge chair frame depicted in FIG. 3B.
Figure 5:
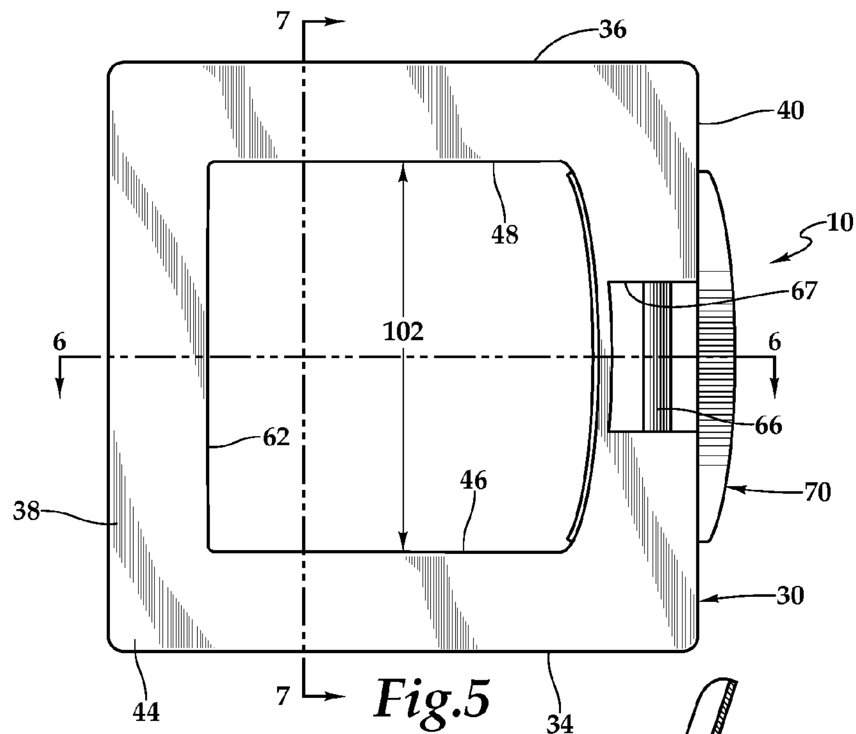
FIG. 5 is bottom plan view of the buoyant pool lounge chair frame depicted in FIG. 3B.
Figure 6:
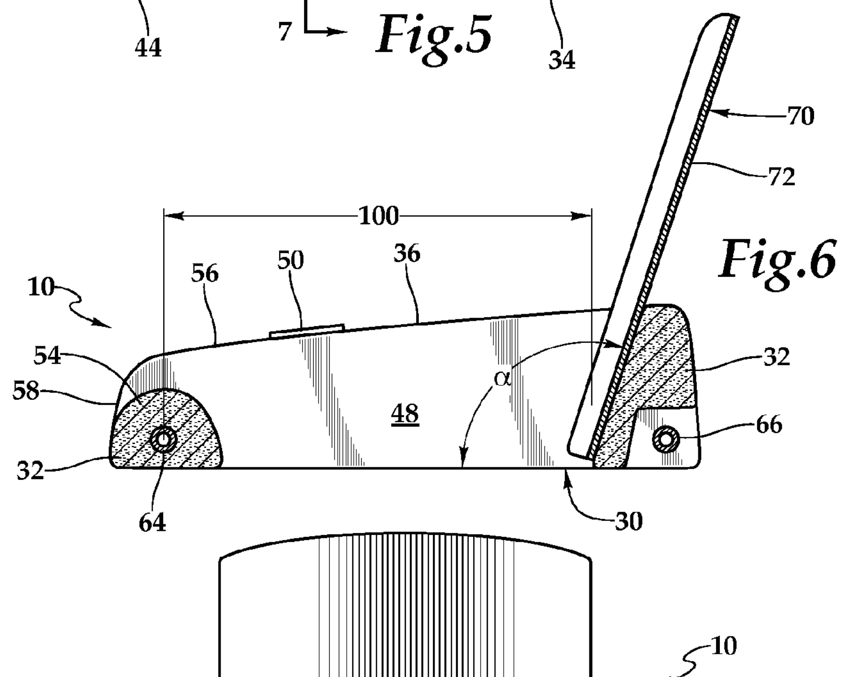
FIG. 6 is a cross-sectional view along line 6-6 of FIG. 5 of the buoyant pool lounge chair frame depicted in FIG. 3B.
Figure 7:
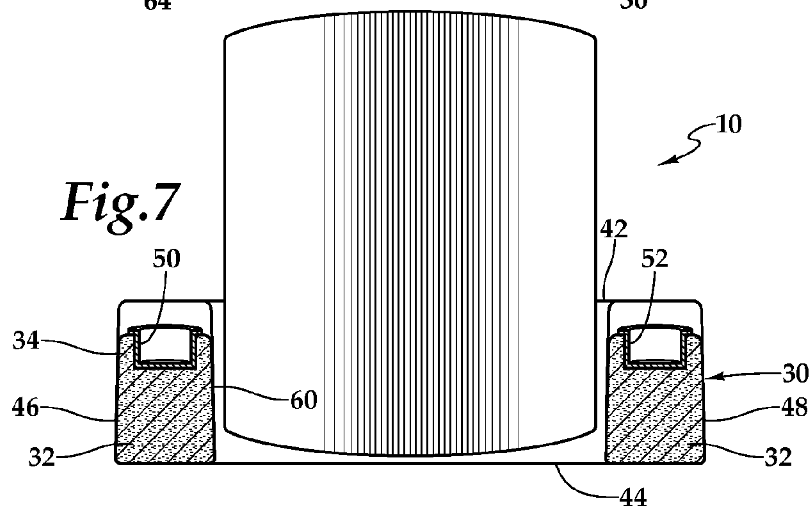
FIG. 7 is a cross-sectional view along line 7-7 of FIG. 5 of the buoyant pool lounge chair frame depicted in FIG. 3B.

In operation, as particularly shown in FIG. 1 and FIG. 2, the pod frame 30 of the buoyant pool lounge chair 10 is sized to accept the flotation device 12 and the flotation device 12 is releasably engageable therewith. More particularly, the substantially inverted parabolic surface 54 and the centra 70 are spaced on opposing ends of the window 60 and configured to be selectively engageable with the floatation device 12 such that the right edge 24 and the left edge 26 of the flotation device 12 may form a friction fit or a slidable engagement with the right and right arm support members 46, 48. The lower side 22 of the floatation device 12 at least partially engages the substantially inverted parabolic surface 54 and the centra 70 in a load-bearing relationship such that a portion of the flotation device 12 is in the water.

As shown, the inverted parabolic surface 54 and the centra 70 are configured to selectively receive the flotation device 12 such that the flotation device forms a wave 80 having a trough 82 at a front of the flotation device 12, a crest 84 at the substantially inverted parabolic surface 54, another trough 86 within the vertical opening 62 between the substantially inverted parabolic surface 54 and the centra 70, and a crest 88 proximate to the centra 70. To further assist the releasably engagement between the flotation device 12 and the buoyant pool lounge chair frame 10 in furtherance of the buoyant pool lounge chair 14, fastener members may be coupled to the flotation device 12 and the buoyant pool lounge chair frame 10. By way of example, fastener members such as hook-and-loop fasteners 90, 92 may be secured to the substantially inverted parabolic surface 54 of the front support portion 38 and the centra 70 to mate with complimentary fastener members on the flotation device 12 and provide releasable engagement therewith.

In the illustrated implementation, the window 60 includes a seating span 100 from the front support portion 38 to the rear support portion 40 of approximately a distance from a popliteal fossa (i.e., rear of the knee) to a pelvic area along a distance of femur. Moreover, the window 60 includes a reach span 102 from the right side 34 to the left side 36 of the pod frame 30 of approximately a shoulder width such that an individual may place his or her arms on the respective right and left arm support members 46, 48.

As constructed, in one embodiment, the buoyant pool lounge chair frame 10 may be designed as a continuous form of pliable foam material of constant or appropriately varying density that varies in thickness to provide the rigid base portion 32 having the coating 45 thereon. The construction may include molded foam being provided by a single molding process, and may include void spaces of select shapes to accommodate the cup holders 50, 52 or cross-bars 64, 66, for example. In one embodiment, the construction includes slabs of closed cell polyurethane foam, such as closed cell polyurethane foam F, having a density in the range of approximately 1 lbs/ft3 (16 kg/m3) to approximately 6 lbs/ft3 (96 kg/m3). In one embodiment, the cross-bars 64, 66 and centra 70 may be constructed of polyvinyl chloride (PVC) material. In the instance of the centra 70, the PVC material may comprise a lightweight yet rigid board of moderately expanded closed-cell PVC extruded in a homogeneous sheet with a low gloss matte finish. Such a closed-cell PVC is old under the brand name SINTRA. In another embodiment, multiple closed-cell PVC boards may be used sandwiched between foam slabs to increase the rigidity of components such as the right arm support member 46, left arm support member 48, and rear support portion 40. The protective coating 45, which is water proof, may be applied by various processes, including dipping and spraying, for example. Further, the pod frame may be made by a partially or fully blow molded process depending on volumes. It should be appreciated that although a particular construction and materials are presented herein, the construction of the buoyant pool lounge chair frame 10 presented herein may vary according to the particular application and other constructions and choices of materials are within the teachings presented herein.

As previously alluded, special care should be taken in the consideration of buoyant lounge chairs to provide sufficient buoyancy material to maintain a stable upright orientation while the occupant is in a semi-reclining orientation following, in the present application, the engagement of the flotation device with the buoyant pool lounge chair frame to provide the buoyant pool lounge chair. Such special care is warranted as any buoyant lounge chair can overturn in response to shifting of its center of buoyancy as the occupant turns or moves about. In one embodiment of the buoyant pool lounge chair frame 10, buoyancy sufficient to support an adult occupant having a body weight of 250 lbs (113 kg) is provided by the construction.

The order of execution or performance of the methods and operations illustrated and described herein is not essential, unless otherwise specified. That is, elements of the methods and flows may be performed in any order, unless otherwise specified, and that the methods may include more or less elements than those disclosed herein. For example, it is contemplated that executing or performing a particular step before, contemporaneously with, or after another step are all possible sequences of execution.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It is, therefore, intended that the appended claims encompass any such modifications or embodiments.

What is claimed is:

1. A buoyant pool lounge chair frame for supporting a floatation device while the buoyant pool chair frame is floating in water, comprising:

a pod frame including a rigid base portion having a right side, a left side, a front support portion, and a rear support portion;

right and left arm support members respectively positioned at the right and left sides of the pod frame;

the front support portion having a substantially inverted parabolic surface;

the pod frame being a substantially half-truncated pyramid having an acute scalene triangle profile from the rear support portion to the front support portion;

the pod frame including a window intersecting the right side, the left side, the front and the rear to provide a vertical opening therethrough;

front and rear cross-bars traversing the span between the right side and left side of the pod frame;

a centra including a rigid back support positioned between the right side and left side of the pod frame and extending from the pod frame proximate the rear support portion;

the pod frame sized to accept a floatation device having a first side, a second side, a first edge and a second edge, the floatation device being defined by a continuous form of pliable foam material; and the substantially inverted parabolic surface and the centra being spaced and configured to be selectively engageable with the floatation device such that the first edge and the second edge form a friction fit with the left and right arm support members, the second side at least partially engages the inverted parabolic surface and the centra in a load-bearing relationship such that a portion of the flotation device is in the water.

2. The buoyant pool lounge chair frame as recited in claim 1, wherein the centra is at least partially integrated with the rear support portion.

3. The buoyant pool lounge chair frame as recited in claim 1, wherein the centra is fully integrated with the rear support portion.

4. The buoyant pool lounge chair frame as recited in claim 1, wherein the centra is releasably coupled to the rear support portion.

5. The buoyant pool lounge chair frame as recited in claim 1, wherein the centra is releasably coupled to the rear support portion by a fastener.

6. The buoyant pool lounge chair frame as recited in claim 5, wherein the fastener comprises a hook-and-loop fastener.

7. The buoyant pool lounge chair frame as recited in claim 1, wherein the window comprises a span from the front support portion to the rear support of approximately a distance from a popliteal fossa to a pelvic area.

8. The buoyant pool lounge chair frame as recited in claim 1, wherein the window comprises a span from the left side to the right side of approximately a shoulder width.

9. The buoyant pool lounge chair frame as recited in claim 1, wherein each of the left and right arm support members further comprises a cup holder.

10. The buoyant pool lounge chair frame as recited in claim 1, further comprising fastener members coupled to the substantially inverted parabolic surface, the fastener members configured to mate with corresponding fastener members associated with the flotation device.

11. The buoyant pool lounge chair frame as recited in claim 1, further comprising fastener members coupled to the centra, the fastener members configured to mate with corresponding fastener members associated with the flotation device.

12. The buoyant pool lounge chair frame as recited in claim 1, wherein the rear cross-bar is at least partially exposed.

13. A buoyant pool lounge chair frame for supporting a floatation device while the buoyant pool chair frame is floating in water, comprising:

a pod frame including a rigid base portion having a right side, a left side, a front support portion, and a rear support portion;

right and left arm support members respectively positioned at the left and right sides of the pod frame;

the front support portion having a substantially inverted parabolic surface;

the pod frame being a substantially half-truncated pyramid having an acute scalene triangle profile from the rear support portion to the front support portion;

the pod frame including a window intersecting the right side, the left side, the front and the rear to provide a vertical opening therethrough;

a centra including a rigid back support positioned between the right side and left side of the pod frame and extending from the pod frame proximate the rear support portion;

the pod frame sized to accept a floatation device having a first side, a second side, a first edge and a second edge, the floatation device being defined by a continuous form of pliable foam material.

14. The buoyant pool lounge chair frame as recited in claim 13, wherein the centra is at least partially integrated with the rear support portion.

15. The buoyant pool lounge chair frame as recited in claim 13, wherein the centra is fully integrated with the rear support portion.

16. The buoyant pool lounge chair frame as recited in claim 13, wherein the centra is releasably coupled to the rear support portion.

17. A buoyant pool lounge chair for supporting an individual while the buoyant pool lounge chair is floating in water, comprising:

a floatation device having a first side, a second side, a first edge and a second edge, the floatation device being defined by a continuous form of pliable foam material, the flotation device being buoyant in water separate and apart from the buoyant pool lounge chair;

a pod frame including a rigid base portion having a right side, a left side, a front support portion, and a rear support portion;

right and left arm support members respectively positioned at the left and right sides of the pod frame;

the front support portion having a substantially inverted parabolic surface;

the pod frame being a substantially half-truncated pyramid having an acute scalene triangle profile from the rear support portion to the front support portion;

the pod frame including a window intersecting the right side, the left side, the front and the rear to provide a vertical opening therethrough;

front and rear cross-bars traversing the span between the left side and right side of the pod frame;

a centra including a rigid back support positioned between the right side and left side of the pod frame and extending from the pod frame proximate the rear support portion;

the pod frame sized to accept the floatation device; and the substantially inverted parabolic surface and the centra being spaced and configured to be selectively engageable with the floatation device such that the first edge and the second edge form a friction fit with the left and right arm support members, the second side at least partially engages the inverted parabolic surface and the centra in a load-bearing relationship such that a portion of the flotation device is in the water, when the buoyant lounge chair is floating in the water.

18. The buoyant pool lounge chair frame as recited in claim 17, wherein the centra is at least partially integrated with the rear support portion.

19. The buoyant pool lounge chair frame as recited in claim 17, wherein the centra is fully integrated with the rear support portion.

20. The buoyant pool lounge chair frame as recited in claim 17, wherein the centra is releasably coupled to the rear support portion.

* * * * *